United States Patent [19]

Tobler

[11] Patent Number: 5,077,439

[45] Date of Patent: Dec. 31, 1991

[54] PROCESS FOR THE PREPARATION OF HALO-ALIPHATIC ALDEHYDES

[75] Inventor: Hans Tobler, Allschwil, Switzerland

[73] Assignee: Ciba-Geigy Corporation, Ardsley, N.Y.

[21] Appl. No.: 667,719

[22] Filed: Mar. 11, 1991

Related U.S. Application Data

[62] Division of Ser. No. 471,174, Jan. 26, 1990, Pat. No. 5,026,916.

[30] Foreign Application Priority Data

Feb. 2, 1989 [CH] Switzerland ............................ 366/89

[51] Int. Cl.[5] ............................................ C07C 47/114
[52] U.S. Cl. ...................................................... 568/495
[58] Field of Search ................................ 568/448, 495

[56] References Cited

U.S. PATENT DOCUMENTS

| 3,721,711 | 3/1973 | Maravitz ............................ 260/566 |
| 3,873,624 | 3/1975 | Mathew et al. .................... 260/601 |
| 4,909,835 | 3/1990 | Tobler ................................ 71/103 |
| 4,968,836 | 11/1990 | Känel et al. ...................... 562/108 |
| 5,015,780 | 5/1991 | Steiner et al. ..................... 568/490 |

FOREIGN PATENT DOCUMENTS

| 0243313 | 10/1947 | European Pat. Off. . |
| 2120908 | 11/1971 | Fed. Rep. of Germany . |
| 0619441 | 9/1980 | Switzerland ........................ 568/495 |

OTHER PUBLICATIONS

Reuss et al. J. Org. Chem. vol. 39 #12 (1974).
Wong J. Org. Chem (1983) 3493-3497.
Bloch, Synthesis pp. 140-142 (1978).
Grundke Chem. Ber. 118 4288-4291 (1985).

*Primary Examiner*—Werren B. Lone

*Attorney, Agent, or Firm*—Kevin T. Mansfield; Edward McC. Roberts

[57] ABSTRACT

Compounds of formula I

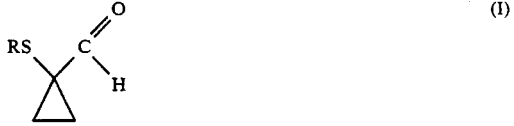

wherein R is $C_1$–$C_4$alkyl or benzyl, are prepared by reacting a butanal of formula II

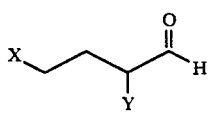

wherein X and Y are each independently of the other chloro, bromo or iodo, in an inert solvent, with a compound of formula III R-S-Me                      (III)

wherein R is as defined above and Me is an alkali metal cation, and converting the resultant compound of formula IV

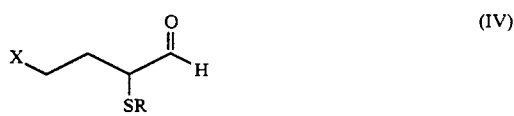

wherein X and R are as defined above, in an inert solvent and in the presence of a base, into a compound of formula I.

3 Claims, No Drawings

PROCESS FOR THE PREPARATION OF HALO-ALIPHATIC ALDEHYDES

This is a divisional of Ser. No. 471,174 filed Jan. 26, 1990, U.S. Pat. No. 5,026,916.

The present invention relates to a novel process for the preparation of 1-alkylthio- and 1-benzylthio-1-formylcyclopropanes of formula I

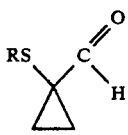

wherein R is $C_1$–$C_4$alkyl or benzyl.

Alkyl will be understood as meaning linear or branched alkyl. Suitable $C_1$–$C_4$alkyl radicals are typically methyl, ethyl, n-propyl, isopropyl, n-butyl or the butyl isomers.

The 1-alkylthio- and 1-benzylthio-1-formylcyclopropanes of formula I are useful intermediates for the synthesis of the herbicidal acylcyclohexanediones disclosed, for example, in European patent application 0 243 313.

In German Offenlegungsschrift 2 120 908 it is taught to prepare 1-methylthio-1-formylcyclopropanes by a) reacting methylthioacetonitrile, in the presence of sodium amide, with 1,2-dibromoethene to give 1-cyano-1-methylthiocyclopropane of formula V

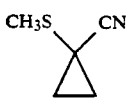

b) converting said compound of formula (V) with concentrated hydrochloric acid to the corresponding cyclopropanecarboxylic acid of formula VI

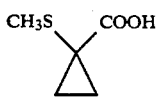

c) reacting the carboxylic acid of formula VI with thionyl chloride to the acid chloride of formula VII

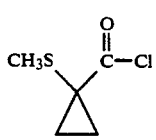

d) reacting the acid chloride so obtained with ethyleneimine and triethylamine to the amide of formula VIII

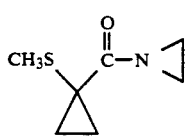

and, finally, e) reacting the amide of formula VIII with lithium aluminium hydride to give the final product, 1-formyl-1-methylthiocyclopropane.

The yields obtainable in this known process are very low. For example, in process step a) the compound of formula V is obtained only in a yield of 16.8%. Based on the starting methylthioacetonitrile, the yield of final product in this five-step process is only ca. 4%.

Aside from the unsatisfactory yield for large-scale production, the large number of synthesis and working up steps make this process very time-consuming and cost-intensive.

There has now been found a novel process which makes it possible to prepare 1-alkylthio- and 1-benzylthio-1-formylcyclopropanes in particularly simple manner and in high yield and good purity.

The process of this invention for the preparation of compounds of formula I

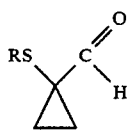

wherein R is $C_1$–$C_4$alkyl or benzyl, comprises reacting a butanal of formula II

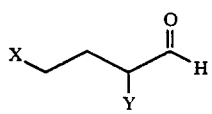

wherein X and Y are each independently of the other chloro, bromo or iodo, in an inert solvent, with a compound of formula III

wherein R is as defined above and Me is an alkali metal cation, and converting the resultant compound of formula IV

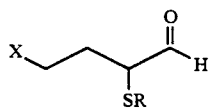

wherein X and R are as defined above, in an inert solvent and in the presence of a base, into a compound of formula I.

Illustrative of suitable solvents for the process of this invention are compounds or mixtures selected from the group of open-chain and cyclic ethers such as dioxane, tetrahydrofuran, diethyl ether, diisopropyl ether, dimethoxymethane and 1,2-dimethoxyethane, or from the group of the alcohols such as methanol, ethanol, propanol, isopropanol and butanol, or water. Methanol, tetrahydrofuran and water have been found to be particularly suitable solvents.

As already described above, Me is an alkali metal, and is preferably lithium, sodium or potassium.

Suitable bases are typically oxides, hydroxides, carbonates, carboxylates or alcoholates of an alkali metal or alkaline earth metal. Sodium methylate, sodium hydroxide, potassium hydroxide, sodium carbonate or potassium carbonate have been found to be especially suitable. The most preferred base is sodium methylate, sodium hydroxide or potassium hydroxide.

The process of this invention can be carried out within a wide temperature range. A temperature range from $-10°$ to $+100°$ C. has been found very suitable. A preferred temperature range is from $-10°$ to $+50°$ C.

The thiol salts of formula III may be used direct and also produced in situ. For example, sodium thiomethylate can be produced by passing methyl mercaptan into an aqueous solution of sodium hydroxide.

The starting compounds of formula II are novel and are likewise an object of the invention. They can be prepared from the corresponding 4-halobutanals by methods analogous to those known in the literature. Examples of such syntheses will be found in the following publications:

J. Org. Chem. (1974), 39, 1785;
Chem. Ber. (1985), 118, 4288;
Synthesis (1978), 140;
J. Org. Chem. (1983), 48, 3493;
Synthesis (1986), 678.

The intermediates of formula IV are novel compounds and constitute a further object of the invention.

The process of this invention can be carried out with as well as without isolation of the intermediates of formula IV.

A preferred variant of the process of this invention comprises reacting the compound of formula II with the compound of formula III, without isolation of the intermediate of formula IV, in an inert solvent and in the presence of a base, to give the compound of formula I.

Starting materials of formula II which are especially suitable for the synthesis of the compounds of formula I are those in which X is chloro and Y is chloro or bromo. Particularly suitable compounds of formula II are those wherein X and Y are chloro.

A particularly preferred variant of the process of this invention comprises reacting a compound of formula II, wherein X is chloro and Y is chloro or bromo, direct with sodium thiomethylate, in the temperature range from $-10°$ C. to $+50°$ C., and in the presence of aqueous sodium hydroxide, in a one pot reaction.

The compounds of formula I may be obtained in the process of this invention in particularly simple manner and in high purity and good yield. The single step or—if isolation of the intermediate of formula IV is desired—two-step mode of carrying out the process eliminates the numerous time-consuming processing steps of the known process, which normally result in losses in yield.

The invention is illustrated by the following non-limitative Examples.

PREPARATORY EXAMPLES

Example 1: Preparation of 2-bromo-4-chlorobutanal (compound 1.1)

With efficient stirring, 12 ml of a 33% solution of hydrogen bromide in acetic acid are added dropwise to a suspension of 120 g of 4-chlorobutanal and 130 g of 5,5-dibromobarbituric acid in 600 ml of diethyl ether, the temperature rising to 35° C. upon onset of the reaction. After 3 to 4 hours, the reaction mixture, which has cooled to room temperature, is filtered. The filtrate is subsequently washed in succession with a dilute solution of sodium hydrogen carbonate and with a saturated solution of sodium chloride until neutral, and dried over sodium sulfate. The solvent is removed by evaporation at 40° C., affording 133 g of 2-bromo-4-chlorobutanal in a yield of 70% of theory and in 93% purity. After purification by distillation at a pressure of 1900 Pa, the boiling point is 74°–75° C.

Example 2: Preparation of 2,4-dichlorobutanal (compound 1.2)

While cooling with ice, 270 g of sulfuryl chloride are added dropwise over 75 minutes to a solution of 237 g of 4-chlorobutanal (90%) in 80 ml of dichloromethane. During this addition, the temperature of the reaction mixture is 10°–20° C. The reaction mixture is then kept for 30 minutes at 5°–10° C., and subsequently refluxed for 2 hours until the evolution of gas ceases. The reaction product is finally obtained by fractional distillation over a 40 cm packed column at 6000 Pa in a yield of 221 g. Boiling point: 90° C. Purification by superfractionation at 9000 Pa over a 20 cm packed column gives 194.1 g (54.7% of theory) of 2,4-dichlorobutanal in 79.5% purity. Boiling point: 96°–99° C.

Example 3: Preparation of 4-chloro-2-iodobutanal (compound 1.3)

1.5 ml of 57% hydriodic acid are added to a suspension of 59.1 g of 4-chlorobutanal (90%), 68 g of mercury(II) chloride and 127 g of iodine in 500 ml of dichloromethane, and the reaction mixture is stirred for 24 hours under reflux. During this time, hydrogen chloride evolves slowly from the reaction mixture, accompanied by the formation of red mercury(II) iodide. The reaction solution is filtered and the filtrate is washed twice with sodium thiosulfate solution and once with a solution of potassium iodide and sodium hydrogen carbonate. After drying over magnesium sulfate, the filtrate is concentrated by evaporation and the residue is fractionated over a 30 cm packed column, affording 85.3 g of 4-chloro-2-iodobutanal in the form of a yellowish red oil in a yield of 61% of theory and a purity of 84%. The boiling point is 46°–47° C./1.3 Pa.

Example 4: Preparation of 2,4-dibromobutanal (compound 1.4)

With efficient stirring, 1.4 ml of a 33% solution of hydrogen bromide in acetic acid are added dropwise to a suspension of 70 g of 4-bromobutanal (98.8%) and 65.6 g of 5,5-dibromobarbituric acid in 300 ml of diethyl ether. The temperature of the reaction mixture rises over 2 hours to 31° C. After a further 2 hours, the reaction mixture has cooled again to room temperature. The mixture is cooled to 0° C. and filtered. The filtrate is then washed 3 times with a saturated solution of sodium chloride and a small amount of sodium hydrogen carbonate solution. The filtrate is dried over magnesium sulfate and the solution is concentrated by evaporation, affording 90 g of a pale yellow oil in 91.1% purity.

Working up of the crude product by distillation over a Vigreux column at 1.3 Pa gives 39.7 g of 2,4-dibromobutanal (34% of theory) in the form of a colourless, slightly mobile oil in 92% purity. Boiling point: 42°–45° C.

The following compounds of formula II are also obtained in accordance with the procedure described above:

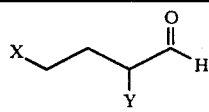

| Compound | X  | Y  |
|----------|----|----|
| 1.5      | Br | Cl |
| 1.6      | Br | J  |
| 1.7      | J  | Cl |
| 1.8      | J  | Br |
| 1.9      | J  | J  |

Example 5: Preparation of 4-chloro-2-methylthiobutanal (compound (3.1)

A solution of 26.2 g of sodium thiomethylate in 170 ml of methanol are added dropwise at a temperature of −5° C. over 20 minutes to 54.8 g of freshly distilled 2,4-dichlorobutanal (96%) in 100 ml of tetrahydrofuran. The reaction mixture is kept for 18 hours at room temperature, then diluted with diethyl ether and thereafter extracted with water. The organic phase is then washed twice with a saturated solution of sodium chloride and once with a solution of sodium hydrogen carbonate, dried over magnesium sulfate and concentrated over a column under atmospheric pressure. The reaction mixture is then distilled over a 30 cm packed column at 2600 Pa, giving 6.7 g of 4-chloro-2-methylthiobutanal (compound 3.1) in the form of a colourless oil which boils at 104° C./2600 Pa.

Example 6: Preparation of 1-formyl-1-methylthiocyclopropane (compound 2.1)

15 ml of a 3N aqueous solution of sodium hydroxide are added at 25° C. to 6 g of 4-chloro-2-methylthiobutanal (compound 3.1) in 2 ml of methanol. The reaction mixture is stirred for 35 minutes and then extracted twice with diethyl ether, and the extracts are washed with a saturated solution of sodium chloride. The combined organic phases are dried over magnesium sulfate. The solution is concentrated over a column under atmospheric pressure, and the residue is then distilled in a bomb tube under atmospheric pressure at 150°-200° C., giving 2.4 g of 1-formyl-1-methylthiocyclopropane (compound 2.1) in the form of an oil.

Example 7: Preparation of 1-formyl-1-methylthiocyclopropane (compound 2.1)

A solution of 58.6 g of 2-bromo-4-chlorobutanal (freshly distilled, 95%) in 50 ml of methanol is prepared while cooling with ice. With cooling, 22.4 g of 94% sodium thiomethylate in 130 ml of methanol are then added dropwise to this solution over 15 minutes. During this addition, the temperature of the reaction mixture is 20°-23° C. After 15 minutes, 54 g of a 30% solution of sodium methylate in methanol are added dropwise over 1 to 2 minutes to the 4-chloro-2-methylthiobutanal obtained as intermediate (compound 3.1). During this addition, the temperature of the reaction mixture rises to 30° C. After the reaction has subsided, water is added and the mixture is extracted three times with diethyl ether. The combined organic phases are washed with a saturated solution of sodium chloride and subsequently dried over magnesium sulfate. The solution is concentrated under atmospheric pressure over a column, and the residue is fractionated over a packed column, affording 23.8 g (67% of theory) of 1-formyl-1-methylthiocyclopropane in 98% purity.
Boiling point: 88°-91° C. at 9 600 to 10 000 Pa.

Example 8: Preparation of 1-formyl-1-methylthiocyclopropane (compound 2.1.)

While cooling with ice, 38 g of sodium thiomethylate are added in portions over 30 minutes to a solution of 81 g of 2,4-dichlorobutanal (92%) in 300 ml of tetrahydrofuran, whereupon the intermediate, 4-chloro-2-methylthiobutanal, forms (compound 3.1). The reaction mixture is kept for 24 hours at room temperature and then, with efficient stirring and intensive cooling, 95.4 g of a 30% solution of sodium methylate in methanol are added at 0° C. over 15 minutes. The reaction mixture is then allowed to warm to room temperature. After extraction by addition of 250 ml of water and 250 ml of diethyl ether, the aqueous phase is separated and extracted a second time with 250 ml of diethyl ether. The combined organic phases are subsequently washed with two 250 ml portions of saturated sodium chloride solution and dried over magnesium sulfate. The solution is concentrated under atmospheric pressure over a column. Fractionation of the residue over a 30 cm packed column gives 30.5 g (47% of theory) of 1-formyl-1-methylthiocyclopropane in 97% purity. Boiling point: 92° C. at 10,200–10,400 Pa.

Example 9: Preparation of 1-formyl-1-methylthiocyclopropane (compound 2.1)

720 g of a 30% solution of sodium methylate in methanol (2 eq.) are diluted with 100 ml of methanol. While cooling with ice/sodium chloride, 90 g of methyl mercaptan are passed into this solution at 0°-5° C., whereupon sodium thiomethylate forms. Then 264 g of freshly distilled 2,4-dichlorobutanal are added dropwise over 20 minutes to the reaction solution, whereupon sodium chloride precipitates immediately and the temperature of the reaction mixture rises to 37° C. After 90 minutes, the reaction mixture is extracted by addition of 1 liter of water and 1 liter of diethyl ether. The organic phase is then separated, and the aqueous phase is extracted with another four 250 ml portions of diethyl ether. The combined organic phases are washed with a saturated solution of sodium chloride and dried over magnesium sulfate. The reaction mixture is concentrated under atmospheric pressure over a packed column. Fractional distillation of the residue over a 40 cm packed column gives 168 g (75% of theory) of 1-formyl-1-methylthiocyclopropane in 97% purity. Boiling point: 92°-93° C./10 400 Pa.

Example 10: Preparation of 1-formyl-1-methylthiocyclopropane (compound 2.1)

With stirring, 120.3 g of sodium thiomethylate (97%) are added to a solution of 107.5 g of pulverised potassium hydroxide (86%) in 600 ml of methanol. The clear, yellowish solution is cooled to 15° C., and then a solution of 230 g of 2,4-dichlorobutanal (98%) in 200 ml of tetrahydrofuran is added dropwise over 25 minutes while cooling with ice. During this addition, the temperature of the reaction mixture is 30°-40° C. After 1 hour, 1 liter of water is added and the reaction mixture is extracted with four 300 ml portions of diethyl ether. The combined organic extracts are washed with a saturated solution of sodium chloride and dried over magnesium sulfate. The reaction solution is then concentrated under atmospheric pressure over a packed column. Fractional distillation of the residue under reduced pressure over a 40 cm packed column gives 135.8 g of 1-formyl-1-methylthiocyclopropane (71.8% of theory) in 99% purity. Boiling point: 89°-91° C./9 600 Pa.

Example 11: Preparation of 1-formyl-1-methylthiocyclopropane (compound 2.1)

While cooling with ice/sodium chloride, 70 g (1 eq.) of methyl mercaptan are passed into a solution of 116.3 g (2 eq.) of sodium hydroxide in 750 ml of water. While maintaining the cooling and with efficient stirring, 188.6 g of freshly distilled 2,4-dichlorobutanal (97%) are added dropwise over 100 minutes. During this addition, the temperature of the reaction mixture rises from 2° C. to 8°-9° C. After 1 hour, the reaction mixture is extracted with four 250 ml portions of diethyl ether. The combined organic phases are washed with a saturated solution of sodium chloride until neutral, dried over magnesium sulfate, and the solution is concentrated under atmospheric pressure over a packed column. Fractional distillation of the residue under reduced pressure over a 40 cm packed column gives 126 g of 1-formyl-1-methylthiocyclopropane (85% of theory) in 99% purity. Boiling point: 91°-92° C./10 000 Pa.

Example 12: Preparation of 1-formyl-1-tert-butylthiocyclopropane (compound 2.2)

Under an atmosphere of nitrogen and while cooling with ice, 112 ml of tert-butyl mercaptan are added dropwise over 10 minutes to a solution, cooled to 5° C., of 80 g of sodium hydroxide in 750 ml of water. Then 50 ml of methanol are added. After 1 hour, 151 g of 2-bromo-4-chlorobutanal (89.5%) are added dropwise over 15 minutes with efficient stirring and cooling, whereupon the temperature of the reaction mixture rises from 5° to 20° C. After 30 minutes, the mixture is extracted 4 times with diethyl ether. The combined organic phases are washed twice with a saturated solution of sodium chloride and dried over magnesium sulfate. The residue obtained after concentrating the residue on a rotary evaporator is fractionated over a 30 cm packed column, affording 89 g of 1-formyl-1-tert-butylthiocyclopropane in 89% purity. Boiling point: 112°-114° C./8 400 Pa.

The following compounds of formula I are also obtained in accordance with the foregoing procedures:

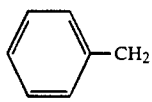
(I)

| Compound | R | Boiling point/Pressure |
|---|---|---|
| 2.3 | $C_2H_5$ | +57 to +58° C./1800 Pa |
| 2.4 | $C_3H_7$-n | +74 to +76° C./2000 Pa |

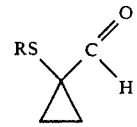
(I)

| Compound | R | Boiling point/Pressure |
|---|---|---|
| 2.5 | $C_3H_7$-i | +67 to +68° C./2000 Pa |
| 2.6 | $C_4H_9$-n | 2.6 |
| 2.7 | $C_4H_9$-i | 2.7 |
| 2.8 | $C_4H_9$-sec. | 2.8 |
| 2.9 | 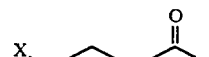 | +90 to +91° C./1.3 Pa |

The following intermediates of formula IV are also obtained in accordance with the procedures described in Examples 5, 7 and 8:

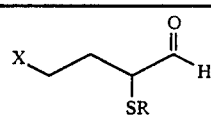
(IV)

| Compound | X | R | Boiling point/Pressure |
|---|---|---|---|
| 3.2 | Cl | $C_2H_5$ | |
| 3.3 | Cl | $C_3H_7$(n) | |
| 3.4 | Cl | $C_3H_7$(iso) | |
| 3.5 | Cl | $C_4H_9$(n) | |
| 3.6 | Cl | $C_4H_9$(sec.) | |
| 3.7 | Cl | $C_4H_9$(tert.) | |
| 3.8 | Cl | $C_4H_9$(iso) | |
| 3.9 | Br | $CH_3$ | |
| 3.10 | Br | $C_2H_5$ | |
| 3.11 | Br | $C_3H_7$(n) | |
| 3.12 | Br | $C_3H_7$(iso) | |
| 3.13 | Br | $C_4H_9$(n) | |
| 3.14 | Br | $C_4H_9$(sec.) | |
| 3.15 | Br | $(C_4H_9$(iso) | |
| 3.16 | Br | $C_4H_9$(tert.) | |
| 3.17 | I | $CH_3$ | |
| 3.18 | I | $C_2H_5$ | |
| 3.19 | I | $C_3H_7$(n) | |
| 3.20 | I | $C_3H_7$(iso) | |
| 3.21 | I | $C_4H_9$(n) | |
| 3.22 | I | $C_4H_9$(sec.) | |
| 3.23 | I | $(C_4H_9$(iso) | |
| 3.24 | I | $C_4H_9$(tert.) | |

What is claimed is:

1. A compound of formula II $$X\diagdown\diagup\diagdown_{Y}\diagup^{O}_{H} \quad (II)$$

wherein X and Y are each independently of the other chloro, bromo or iodo.

2. A compound of formula II according to claim 1, wherein X is chloro and Y is chloro or bromo.

3. A compound of formula II according to claim 1, wherein X and Y are chloro.

* * * * *